United States Patent
Dean

(10) Patent No.: US 6,235,723 B1
(45) Date of Patent: *May 22, 2001

(54) ANTISENSE OLIGONUCLEOTIDE MODULATION OF HUMAN PROTEIN KINASE C-δ EXPRESSION

(75) Inventor: Nicholas M. Dean, Olivenhain, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/313,930

(22) Filed: May 18, 1999

Related U.S. Application Data

(63) Continuation-in-part of application No. 08/481,072, filed on Jun. 7, 1995, now Pat. No. 5,916,807, and a continuation-in-part of application No. 08/488,177, filed on Jun. 7, 1995, now Pat. No. 5,885,970, and a continuation-in-part of application No. 08/481,066, filed on Jun. 7, 1995, now Pat. No. 5,959,096, and a continuation-in-part of application No. 08/478,178, filed on Jun. 7, 1995, now Pat. No. 5,882,927, and a continuation-in-part of application No. 08/664,336, filed on Jun. 14, 1996, now Pat. No. 5,922,686, which is a continuation-in-part of application No. 08/089,996, filed on Jul. 9, 1993, now Pat. No. 5,703,054, which is a continuation-in-part of application No. 07/852,852, filed on Mar. 16, 1992, now abandoned, which is a continuation-in-part of application No. 08/601,269, filed on Feb. 14, 1996, now Pat. No. 5,948,898, which is a continuation-in-part of application No. 08/478,178, filed on Jun. 7, 1995, now Pat. No. 5,882,927, which is a continuation-in-part of application No. 08/089,996, filed on Jul. 9, 1993, now Pat. No. 5,703,054, which is a continuation-in-part of application No. 07/852,852, filed on Mar. 16, 1992, now abandoned.

(51) Int. Cl.$^7$ ............................. A01N 43/04; C12P 19/34; C07H 21/02; C07H 21/04; C12Q 1/68
(52) U.S. Cl. ..................... 514/44; 536/24.5; 536/23.1; 435/6; 435/91.1; 435/455
(58) Field of Search .................. 435/6, 91.1, 91.31, 435/91.51, 375, 377, 455, 366; 536/23.1, 24.5, 25.3, 25.6; 514/44

(56) References Cited

U.S. PATENT DOCUMENTS

| | | | |
|---|---|---|---|
| 5,885,970 | * 3/1999 | Bennett et al. | 514/44 |
| 5,916,807 | * 6/1999 | Bennett et al. | 435/375 |
| 5,959,096 | * 9/1999 | Bennett et al. | 536/24.5 |

FOREIGN PATENT DOCUMENTS

| | | |
|---|---|---|
| WO93/20101 | 10/1993 | (WO) . |
| WO94/29455 | 12/1994 | (WO) . |

OTHER PUBLICATIONS

Branch, A. 1998 Trends in Bioch. Sci. (TIBS) vol. 23, pp. 45–50.*

Crooke, S. T. 1998 Antisense Research & Techniques, Ch. 1, pp. 1–50 (Publisher: Springer–Verlag).*

James, W. 1991. Antiviral Chemistry & Chemotherapy vol. 2 (4), pp. 191–214.*

Shibahara, S. et al. 1989. Nucleic Acids Res. vol. 17(1), pp. 239–252.*

Borek, C., et al., "Long–chain (sphingoid) bases inhibit multistage carcinogenesis in mouse C3H/10T1/2 cells treated with radiation and phorbol 12–myristate 13–acetate", *Proc. Natl. Acad. Sci.* USA 1991 88, 1953–1957.

Busuttil, et al., "Antisense Suppression of Protein Kinase C–α and –δ in Vascular Smooth Muscle", *J. Surg. Res.* 1996 63, 137–142.

Endo, et al., "Cell Membrane Signaling as Target in Cancer Therapy: Inhibitory Effect of N, N–Dimethyl and N,N, N–Trimethyl Sphingosine Derivatives on in Vitro and in Vivo Growth of Human Tumor Cells in Nude Mice[1]", *Cancer Research* 1991 51 1613–1618.

Gamard, D. J., et al., "Specific Role for Protein Kinase C β in Cell Differentiation[1]", *Cell Growth Diff.* 1994 5, 405–409.

Gescher, A., et al., "Protein kinase C–a novel target for rational anti–cancer drug design?", *Anti–Cancer Drug Design* 1989 4, 93–105.

Gschwendt, M., et al., "Rottlerin, A Novel Protein Kinase Inhibitor", *Biochem. Biophys. Res. Commun.* 1994 199, 93–98.

Hegemann, L., et al., "Biochemical Pharmacology of Protein Knase C and its Relevance for Dermatology", *Pharmacology of the Skin*, H. Mukhtar, ed. 1992 357–369 CRC Press, Boca Raton, FL.

Hidaka and Hagiwara, "Pharmacology of the isoquinoline sulfonamide protein kinase C inhibitors", *Trends in Phar. Sci.* 1987 8, 162–164.

Liao, D. F., et al., "Protein Kinase C–ζ Mediates Angiotensin II Activation of ERK1/2 in Vascular Smooth Muscle Cells", *J. Biol. Chem.* 1997 272, 6146–6150.

Liedtke, C.M., et al., "Antisense oligodeoxynucleotide to PKC–δ blocks α$_1$–adrenergic activation of Na–K–2Cl cotransport", *Am J. Physiol.* 1997 273 C1632–C1640.

(List continued on next page.)

*Primary Examiner*—George C. Elliott
*Assistant Examiner*—Jane Zara
(74) *Attorney, Agent, or Firm*—Law Offices of Jane Massey Licata

(57) ABSTRACT

Compositions and methods are provided for modulating the expression of PKC-δ and for the treatment and diagnosis of diseases associated with protein kinase C-δ. Methods of treating animals suffering from disease amenable to therapeutic intervention by modulating protein kinase C-δ expression with an oligonucleotide specifically hybridizable with RNA or DNA corresponding to PKC-δ are disclosed. Methods of modulating the expression of TNF-a using the compositions of the present invention are also provided.

15 Claims, No Drawings

OTHER PUBLICATIONS

McGraw, K., et al., "Antisense oligonucleotide inhibitors of isozymes of protein kinase C: in vitro and in vivo activity, and clinical development as anti-cancer therapeutics", *Anti--Cancer Drug Design* 1997 12, 315–326.

Pessino et al., "Antisense oligodeoxynucleotide inhibition of δ protein kinase C expression accelerates induced differentiation of murine erythroleukaemia cells", *Biochem. J.* 1995 312, 549–554.

Suganuma, M., "A New Process of Cancer Prevention Mediated through Inhibition of Tumor Necrosis Factor α Expression[1]", *Cancer Res.* 1996 56, 3711–3715.

Traub, O., et al., "PKC-ε Is Required for Mechano-sensitive Activation of ERK1/2 in Endothelial Cells", *J. Biol. Chem.* 1997 272, 31251–31257.

* cited by examiner

SEQUENCE LISTING

```
<160> NUMBER OF SEQ ID NOS: 20

<210> SEQ ID NO 1
<211> LENGTH: 2104
<212> TYPE: DNA
<213> ORGANISM: Homo sapiens
<220> FEATURE:
<221> NAME/KEY: CDS
<222> LOCATION: (59)..(2089)
<300> PUBLICATION INFORMATION:
<301> AUTHORS: Aris, J . P.
      Basta, P. V.
      Holmes, W. D.
      Ballas, L. M.
      Moomaw, C.
      Rankl, N. B.
      Blobel, G.
      Loomis, C. R.
      Burns, D. J.
<302> TITLE: Molecular and biochemical characterization of a
      recombinant human PKC-delta family member
<303> JOURNAL: Biochim. Biophys. Acta
<304> VOLUME: 1174
```

```
<305> ISSUE: 2
<306> PAGES: 171-181
<307> DATE: 1993-08-19
<308> DATABASE ACCESSION NUMBER: L07860
<309> DATABASE ENTRY DATE: 1993-11-02

<400> SEQUENCE: 1
tgccgccgcg acccttggcg cctgccctg caacgggagc cccactgcag gccccacc        58 atg gcg ccg ttc ctg cgc atc gcc ttc aac tcc tat gag ctg ggc tcc     106
Met Ala Pro Phe Leu Arg Ile Ala Phe Asn Ser Tyr Glu Leu Gly Ser
 1               5                  10                  15 ctg cag gcc gag gac gag gcg aac cag ccc ttc tgt gcc gtg aag atg     154
Leu Gln Ala Glu Asp Glu Ala Asn Gln Pro Phe Cys Ala Val Lys Met
             20                  25                  30 aag gag gcg ctc agc aca gag cgt ggg aaa aca ctg gtg cag aag aag     202
Lys Glu Ala Leu Ser Thr Glu Arg Gly Lys Thr Leu Val Gln Lys Lys
         35                  40                  45 ccg acc atg tat cct gag tgg aag tcg acg ttc gat gcc cac atc tat     250
Pro Thr Met Tyr Pro Glu Trp Lys Ser Thr Phe Asp Ala His Ile Tyr
     50                  55                  60 gag ggg cgc gtc atc cag att gtg cta atg cgg gca gca gag gag cca     298
Glu Gly Arg Val Ile Gln Ile Val Leu Met Arg Ala Ala Glu Glu Pro
 65                  70                  75                  80 gtg tct gag gtg acc gtg ggt gtg tcg gtg ctg gcc gag cgc tgc aag     346
Val Ser Glu Val Thr Val Gly Val Ser Val Leu Ala Glu Arg Cys Lys
                 85                  90                  95 aag aac aat ggc aag gct gag ttc tgg ctg gac ctg cag cct cag gcc     394
Lys Asn Asn Gly Lys Ala Glu Phe Trp Leu Asp Leu Gln Pro Gln Ala
            100                 105                 110 aag gtg ttg atg tct gtt cag tat ttc ctg gag gac gtg gat tgc aaa     442
Lys Val Leu Met Ser Val Gln Tyr Phe Leu Glu Asp Val Asp Cys Lys
        115                 120                 125 caa tct atg cgc agt gag gac gag gcc aag ttc cca acg atg aac cgc     490
Gln Ser Met Arg Ser Glu Asp Glu Ala Lys Phe Pro Thr Met Asn Arg
    130                 135                 140 cgc gga gcc atc aaa cag gcc aaa atc cac tac atc aag aac cat gag     538
Arg Gly Ala Ile Lys Gln Ala Lys Ile His Tyr Ile Lys Asn His Glu
145                 150                 155                 160 ttt atc gcc acc ttc ttt ggg caa ccc acc ttc tgt tct gtg tgc aaa     586
Phe Ile Ala Thr Phe Phe Gly Gln Pro Thr Phe Cys Ser Val Cys Lys
                165                 170                 175 gac ttt gtc tgg ggc ctc aac aag caa ggc tac aaa tgc agg caa tgt     634
Asp Phe Val Trp Gly Leu Asn Lys Gln Gly Tyr Lys Cys Arg Gln Cys
            180                 185                 190 aac gct gcc atc cac aag aaa tgc atc gac aag atc atc ggc aga tgc     682
Asn Ala Ala Ile His Lys Lys Cys Ile Asp Lys Ile Ile Gly Arg Cys
        195                 200                 205 act ggc acc gcg gcc aac agc cgg gac act ata ttc cag aaa gaa cgc     730
Thr Gly Thr Ala Ala Asn Ser Arg Asp Thr Ile Phe Gln Lys Glu Arg
    210                 215                 220 ttc aac atc gac atg ccg cac cgc ttc aag gtt cac aac tac atg agc     778
Phe Asn Ile Asp Met Pro His Arg Phe Lys Val His Asn Tyr Met Ser
225                 230                 235                 240 ccc acc ttc tgt gac cac tgc ggc agc ctg ctc tgg gga ctg gtg aag     826
Pro Thr Phe Cys Asp His Cys Gly Ser Leu Leu Trp Gly Leu Val Lys
                245                 250                 255 cag gga tta aag tgt gaa gac tgc ggc atg aat gtg cac cat aaa tgc     874
Gln Gly Leu Lys Cys Glu Asp Cys Gly Met Asn Val His His Lys Cys
            260                 265                 270 cgg gag aag gtg gcc aac ctc tgc ggc atc aac cag aag ctt ttg gct     922
```

```
              Arg Glu Lys Val Ala Asn Leu Cys Gly Ile Asn Gln Lys Leu Leu Ala
                  275                 280                 285 gag gcc ttg aac caa gtc acc cag aga gcc tcc cgg aga tca gac tca        970
Glu Ala Leu Asn Gln Val Thr Gln Arg Ala Ser Arg Arg Ser Asp Ser
    290                 295                 300 gcc tcc tca gag cct gtt ggg ata tat cag ggt ttc gag aag aag acc       1018
Ala Ser Ser Glu Pro Val Gly Ile Tyr Gln Gly Phe Glu Lys Lys Thr
305                 310                 315                 320 gga gtt gct ggg gag gac atg caa gac aac agt ggg acc tac ggc aag       1066
Gly Val Ala Gly Glu Asp Met Gln Asp Asn Ser Gly Thr Tyr Gly Lys
                325                 330                 335 atc tgg gag ggc agc agc aag tgc aac atc aac aac ttc atc ttc cac       1114
Ile Trp Glu Gly Ser Ser Lys Cys Asn Ile Asn Asn Phe Ile Phe His
            340                 345                 350 aag gtc ctg ggc aaa ggc agc ttc ggg aag gtg ctg ctt gga gag ctg       1162
Lys Val Leu Gly Lys Gly Ser Phe Gly Lys Val Leu Leu Gly Glu Leu
        355                 360                 365 aag ggc aga gga gag tac tct gcc atc aag gcc ctc aag aag gat gtg       1210
Lys Gly Arg Gly Glu Tyr Ser Ala Ile Lys Ala Leu Lys Lys Asp Val
    370                 375                 380 gtc ctg atc gac gac gac gtg gag tgc acc atg gtt gag aag cgg gtg       1258
Val Leu Ile Asp Asp Asp Val Glu Cys Thr Met Val Glu Lys Arg Val
385                 390                 395                 400 ctg aca ctt gcc gca gag aat ccc ttt ctc acc cac ctc atc tgc acc       1306
Leu Thr Leu Ala Ala Glu Asn Pro Phe Leu Thr His Leu Ile Cys Thr
                405                 410                 415 ttc cag acc aag gac cac ctg ttc ttt gtg atg gag ttc ctc aac ggg       1354
Phe Gln Thr Lys Asp His Leu Phe Phe Val Met Glu Phe Leu Asn Gly
            420                 425                 430 ggg gac ctg atg tac cac atc cag gac aaa ggc cgc ttt gaa ctc tac       1402
Gly Asp Leu Met Tyr His Ile Gln Asp Lys Gly Arg Phe Glu Leu Tyr
        435                 440                 445 cgt gcc acg ttt tat gcc gct gag ata atg tgt gga ctg cag ttt cta       1450
Arg Ala Thr Phe Tyr Ala Ala Glu Ile Met Cys Gly Leu Gln Phe Leu
    450                 455                 460 cac agc aag ggc atc att tac agg gac ctc aaa ctg gac aat gtg ctg       1498
His Ser Lys Gly Ile Ile Tyr Arg Asp Leu Lys Leu Asp Asn Val Leu
465                 470                 475                 480 ttg gac cgg gat ggc cac atc aag att gcc gac ttt ggg atg tgc aaa       1546
Leu Asp Arg Asp Gly His Ile Lys Ile Ala Asp Phe Gly Met Cys Lys
                485                 490                 495 gag aac ata ttc ggg gag agc cgg gcc agc acc ttc tgc ggc acc cct       1594
Glu Asn Ile Phe Gly Glu Ser Arg Ala Ser Thr Phe Cys Gly Thr Pro
            500                 505                 510 gac tat atc gcc cct gag atc cta cag ggc ctg aag tac aca ttc tct       1642
Asp Tyr Ile Ala Pro Glu Ile Leu Gln Gly Leu Lys Tyr Thr Phe Ser
        515                 520                 525 gtg gac tgg tgg tct ttc ggg gtc ctt ctg tac gag atg ctc att ggc       1690
Val Asp Trp Trp Ser Phe Gly Val Leu Leu Tyr Glu Met Leu Ile Gly
    530                 535                 540 cag tcc ccc ttc cat ggt gat gat gag gat gaa ctc ttc gag tcc atc       1738
Gln Ser Pro Phe His Gly Asp Asp Glu Asp Glu Leu Phe Glu Ser Ile
545                 550                 555                 560 cgt gtg gac acg cca cat tat ccc cgc tgg atc acc aag gag tcc aag       1786
Arg Val Asp Thr Pro His Tyr Pro Arg Trp Ile Thr Lys Glu Ser Lys
                565                 570                 575 gac atc ctg gag aag ctc ttt gaa agg gaa cca acc aag agg ctg gga       1834
Asp Ile Leu Glu Lys Leu Phe Glu Arg Glu Pro Thr Lys Arg Leu Gly
            580                 585                 590
```

```
atg acg gga aac atc aaa atc cac ccc ttc ttc aag acc ata aac tgg      1882
Met Thr Gly Asn Ile Lys Ile His Pro Phe Phe Lys Thr Ile Asn Trp
        595                 600                 605 act ctg ctg gaa aag cgg agg ttg gag cca ccc ttc agg ccc aaa gtg      1930
Thr Leu Leu Glu Lys Arg Arg Leu Glu Pro Pro Phe Arg Pro Lys Val
610                 615                 620 aag tca ccc aga gac tac agt aac ttt gac cag gag ttc ctg aac gag      1978
Lys Ser Pro Arg Asp Tyr Ser Asn Phe Asp Gln Glu Phe Leu Asn Glu
625                 630                 635                 640 aag gcg cgc ctc tcc tac agc gac aag aac ctc atc gac tcc atg gac      2026
Lys Ala Arg Leu Ser Tyr Ser Asp Lys Asn Leu Ile Asp Ser Met Asp
                645                 650                 655 cag tct gca ttc gct ggc ttc tcc ttt gtg aac ccc aaa ttc gag cac      2074
Gln Ser Ala Phe Ala Gly Phe Ser Phe Val Asn Pro Lys Phe Glu His
            660                 665                 670 ctc ctg gaa gat tga ggttcctgga cagat                                 2104
Leu Leu Glu Asp
        675

<210> SEQ ID NO 2
<211> LENGTH: 676
<212> TYPE: PRT
<213> ORGANISM: Homo sapiens

<400> SEQUENCE: 2

Met Ala Pro Phe Leu Arg Ile Ala Phe Asn Ser Tyr Glu Leu Gly Ser
1               5                   10                  15

Leu Gln Ala Glu Asp Glu Ala Asn Gln Pro Phe Cys Ala Val Lys Met
            20                  25                  30

Lys Glu Ala Leu Ser Thr Glu Arg Gly Lys Thr Leu Val Gln Lys Lys
        35                  40                  45

Pro Thr Met Tyr Pro Glu Trp Lys Ser Thr Phe Asp Ala His Ile Tyr
    50                  55                  60

Glu Gly Arg Val Ile Gln Ile Val Leu Met Arg Ala Ala Glu Glu Pro
65              70                  75                  80

Val Ser Glu Val Thr Val Gly Val Ser Val Leu Ala Glu Arg Cys Lys
                85                  90                  95

Lys Asn Asn Gly Lys Ala Glu Phe Trp Leu Asp Leu Gln Pro Gln Ala
            100                 105                 110

Lys Val Leu Met Ser Val Gln Tyr Phe Leu Glu Asp Val Asp Cys Lys
        115                 120                 125

Gln Ser Met Arg Ser Glu Asp Glu Ala Lys Phe Pro Thr Met Asn Arg
    130                 135                 140

Arg Gly Ala Ile Lys Gln Ala Lys Ile His Tyr Ile Lys Asn His Glu
145                 150                 155                 160

Phe Ile Ala Thr Phe Phe Gly Gln Pro Thr Phe Cys Ser Val Cys Lys
                165                 170                 175

Asp Phe Val Trp Gly Leu Asn Lys Gln Gly Tyr Lys Cys Arg Gln Cys
            180                 185                 190

Asn Ala Ala Ile His Lys Lys Cys Ile Asp Lys Ile Ile Gly Arg Cys
        195                 200                 205

Thr Gly Thr Ala Ala Asn Ser Arg Asp Thr Ile Phe Gln Lys Glu Arg
    210                 215                 220

Phe Asn Ile Asp Met Pro His Arg Phe Lys Val His Asn Tyr Met Ser
225                 230                 235                 240

Pro Thr Phe Cys Asp His Cys Gly Ser Leu Leu Trp Gly Leu Val Lys
                245                 250                 255
```

-continued

```
Gln Gly Leu Lys Cys Glu Asp Cys Gly Met Asn Val His His Lys Cys
            260                 265                 270
Arg Glu Lys Val Ala Asn Leu Cys Gly Ile Asn Gln Lys Leu Leu Ala
        275                 280                 285
Glu Ala Leu Asn Gln Val Thr Gln Arg Ala Ser Arg Arg Ser Asp Ser
290                 295                 300
Ala Ser Ser Glu Pro Val Gly Ile Tyr Gln Gly Phe Glu Lys Lys Thr
305                 310                 315                 320
Gly Val Ala Gly Glu Asp Met Gln Asp Asn Ser Gly Thr Tyr Gly Lys
                325                 330                 335
Ile Trp Glu Gly Ser Ser Lys Cys Asn Ile Asn Asn Phe Ile Phe His
                340                 345                 350
Lys Val Leu Gly Lys Gly Ser Phe Gly Lys Val Leu Leu Gly Glu Leu
            355                 360                 365
Lys Gly Arg Gly Glu Tyr Ser Ala Ile Lys Ala Leu Lys Lys Asp Val
        370                 375                 380
Val Leu Ile Asp Asp Asp Val Glu Cys Thr Met Val Glu Lys Arg Val
385                 390                 395                 400
Leu Thr Leu Ala Ala Glu Asn Pro Phe Leu Thr His Leu Ile Cys Thr
                405                 410                 415
Phe Gln Thr Lys Asp His Leu Phe Phe Val Met Glu Phe Leu Asn Gly
                420                 425                 430
Gly Asp Leu Met Tyr His Ile Gln Asp Lys Gly Arg Phe Glu Leu Tyr
            435                 440                 445
Arg Ala Thr Phe Tyr Ala Ala Glu Ile Met Cys Gly Leu Gln Phe Leu
        450                 455                 460
His Ser Lys Gly Ile Ile Tyr Arg Asp Leu Lys Leu Asp Asn Val Leu
465                 470                 475                 480
Leu Asp Arg Asp Gly His Ile Lys Ile Ala Asp Phe Gly Met Cys Lys
                485                 490                 495
Glu Asn Ile Phe Gly Glu Ser Arg Ala Ser Thr Phe Cys Gly Thr Pro
                500                 505                 510
Asp Tyr Ile Ala Pro Glu Ile Leu Gln Gly Leu Lys Tyr Thr Phe Ser
            515                 520                 525
Val Asp Trp Trp Ser Phe Gly Val Leu Leu Tyr Glu Met Leu Ile Gly
        530                 535                 540
Gln Ser Pro Phe His Gly Asp Asp Glu Asp Glu Leu Phe Glu Ser Ile
545                 550                 555                 560
Arg Val Asp Thr Pro His Tyr Pro Arg Trp Ile Thr Lys Glu Ser Lys
                565                 570                 575
Asp Ile Leu Glu Lys Leu Phe Glu Arg Glu Pro Thr Lys Arg Leu Gly
                580                 585                 590
Met Thr Gly Asn Ile Lys Ile His Pro Phe Phe Lys Thr Ile Asn Trp
            595                 600                 605
Thr Leu Leu Glu Lys Arg Arg Leu Glu Pro Pro Phe Arg Pro Lys Val
        610                 615                 620
Lys Ser Pro Arg Asp Tyr Ser Asn Phe Asp Gln Glu Phe Leu Asn Glu
625                 630                 635                 640
Lys Ala Arg Leu Ser Tyr Ser Asp Lys Asn Leu Ile Asp Ser Met Asp
                645                 650                 655
Gln Ser Ala Phe Ala Gly Phe Ser Phe Val Asn Pro Lys Phe Glu His
                660                 665                 670
```

```
Leu Leu Glu Asp
        675
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
gcaggaacgg cgccatggtg                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
ctggttcgcc tcgtcctcgg                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
atctggatga cgcgcccctc                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ttcttgcagc gctcggccag                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
tgcaatccac gtcctccagg                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
aagcggtgcg gcatgtcgat                                                   20

<210> SEQ ID NO 9
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 9
aagcggtgcg gcatgtcgat                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
gcaggctgcc gcagtggtca                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
cctccccagc aactccggtc                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
agcggccttt gtcctggatg                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
ggccatcccg gtccaacagc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
ggtgctggcc cggctctccc                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ggaccccgaa agaccaccag                                              20
```

```
<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
gtggctccaa cctccgcttt                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
aggaggtgct cgaatttggg                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
agcccaccga gacaccgaga                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
aacccatcgg ctggcaccac                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
tcaagcagtg ccaccgatcc                                              20
```

ANTISENSE OLIGONUCLEOTIDE MODULATION OF HUMAN PROTEIN KINASE C-δ EXPRESSION

This application is a continuation-in-part of U.S. patent application Ser. No. 08/481,072, filed Jun. 7, 1995, now issued as U.S. Pat. No. 5,916,807; U.S. patent application Ser. No. 08/488,177, filed Jun. 7, 1995, now issued as U.S. Pat. No. 5,885,970; U.S. patent application Ser. No. 08/481,066, filed Jun. 7, 1995, now issued as U.S. Pat. No. 5,959,096; U.S. patent application Ser. No. 08/478,178, filed Jun. 7, 1995, now issued as U.S. Pat. No. 5,882,927; and U.S. patent application Ser. No. 08/664,336, filed Jun. 14, 1996, now issued as U.S. Pat. No. 5,922,686, which are all continuations-in-part of U.S. patent application Ser. No. 08/089,996, filed Jul. 9, 1993, now issued as U.S. Pat. No. 5,703,054, which in turn is a continuation-in-part of a U.S. patent application Ser. No. 07/852,852, filed Mar. 16, 1992, now abandoned. This application is also a continuation-in-part of U.S. patent application Ser. No. 08/601,269, filed Feb. 14, 1996, now issued as U.S. Pat. No. 5,948,898, which is a continuation-in-part of U.S. patent application Ser. No. 08/478,178, filed Jun. 7, 1995, and now issued as U.S. Pat. No. 5,882,927, which is a continuation-in-part of U.S. patent application Ser. No. 08/089,996, filed Jul. 9, 1993, now issued as U.S. Pat. No. 5,703,054, which in turn is a continuation-in-part of U.S. patent application Ser. No. 07/852,852 filed Mar. 16, 1992, now abandoned.

FIELD OF THE INVENTION

This invention relates to compositions and methods for modulating expression of the human protein kinase C-δ gene, a naturally present cellular gene implicated in signal transduction and cellular differentiation. This invention is also directed to methods for modulating differentiation of cells or expression of tumor necrosis factor α; these methods can be used diagnostically or therapeutically. Furthermore, this invention is directed to treatment of conditions or diseases associated with expression of the human protein kinase C-δ gene or tumor necrosis factor α gene.

BACKGROUND OF THE INVENTION

The protein kinase C (PKC) family comprises serine/threonine kinases involved in signal transduction pathways regulating cell proliferation and differentiation. Chronic activation of PKC results in abnormal cellular proliferation and tumor formation. Interest in PKC was stimulated by the finding that PKC is the major, and perhaps only, cellular receptor through which a class of tumor-promoting agents called phorbol esters exert their pleiotropic effects on cells (Gescher et al., *Anti-Cancer Drug Design*, 1989, 4, 93–105). Phorbols capable of tumor production can mimic the effect of diacylglycerol (DAG) in activating PKC, suggesting that these tumor promoters act through PKC and that activation of this enzyme is at least partially responsible for the resulting tumorigenesis (Parker et al., *Science*, 1986, 233, 853–866).

Increased tumorigenicity is also correlated with overexpression of PKC in cultured cells inoculated into nude mice. A mutant form of PKC induces highly malignant tumor cells with increased metastatic potential. Sphingosine and related inhibitors of PKC activity have been shown to inhibit tumor cell growth and radiation-induced transformation in vivo (Endo et al., *Cancer Research*, 1991, 51, 1613–1618); Borek et al., *Proc. Natl. Acad. Sci.*, 1991, 88, 1953–1957). A number of experimental or clinically useful anti-cancer drugs show modulatory effects on PKC. Therefore, inhibitors of PKC may be important cancer-preventive or therapeutic agents. PKC has been suggested as a plausible target for more rational design of conventional anti-cancer drugs (Gescher, A. and Dale, I. L., *Anti-Cancer Drug Design*, 1989, 4, 93–105).

Experiments also indicate that PKC plays an important role in the pathophysiology of hyperproliferative skin disorders such as psoriasis and skin cancer. Psoriasis is characterized by inflammation, hyperproliferation of the epidermis and decreased differentiation of cells. Various studies indicate a role for PKC in causing these symptoms. PKC stimulation in cultured keratinocytes can be shown to cause hyperproliferation. Inflammation can be induced by phorbol esters and is regulated by PKC. DAG is implicated in the involvement of PKC in dermatological diseases, and is formed to an increased extent in psoriatic lesions.

Inhibitors of PKC have been shown to have both antiproliferative and antiinflammatory effects in vitro. Some antipsoriasis drugs, such as cyclosporine A and anthralin, have been shown to inhibit PKC. Inhibition of PKC has been suggested as a therapeutic approach to the treatment of psoriasis (Hegemann, L. and Mahrle, G., *Pharmacology of the Skin*, H. Mukhtar, ed., 1992, CRC Press, Boca Raton, Fla., p. 357–368).

PKC is not a single enzyme, but a family of enzymes. At the present time at least ten isoforms (isozymes) of PKC have been identified: the "conventional" isoforms α, β, and γ, the "novel" isoforms δ, ε, η, θ and μ, and the "atypical" isoforms ζ and λ. These isozymes have distinct patterns of tissue and organ localization (see Nishizuka, *FASEB J.*, 1995, 9, 484–496 for review) and may serve different physiological functions.

The role of the individual PKC members has been studied by overexpression of the genes and, more recently, using antisense oligonucleotides. Overexpression of PKC-δ has been shown to inhibit cell growth and increased levels are associated with increased tumor potential. For example, PKC-δ is the PKC isoform most represented in murine erythroleukemia (MEL) cells. Incorporation of partially purified PKC-δ protein into permeabilized MEL cells causes a delay in chemically induced differentiation. Thus, it is believed the PKC-δ levels may be important in modulating differentiation in these leukemic cells (Fessino et al., *Biochem J.*, 1995, 312, 549–554). However, growth effects may be dependent upon cell type. Modulation of PKC-δ may be particularly useful in hyperproliferative disorders, particularly hematopoietic diseases, such as acute promyelocytic, leukemia, and skin disorders, such as psoriasis.

According to the present invention, PKC-δ is also able to modulate tumor necrosis factor α expression. Modulation of PKC-δ may, therefore, also be useful in disease states associated with overexpression of TNF-α, particularly infectious, inflammatory and autoimmune diseases. High levels of plasma TNF-α have been found in infectious diseases such as sepsis syndrome, bacterial meningitis, cerebral malaria, and AIDS; autoimmune diseases such as rheumatoid arthritis, inflammatory bowel disease (including Crohn's disease), sarcoidosis, multiple sclerosis, Kawasaki syndrome, graft-versus-host disease and transplant (allograft) rejection; organ failure conditions such as adult respiratory distress syndrome, congestive heart failure, acute liver failure and myocardial infarction (Eigler, A., et al., *Immunol. Today*, 1997, 18, 487–492). Other diseases in which TNF-α is involved include asthma (Shah, A., et al., *Clinical and Experimental Allergy*, 1995, 25, 1038–1044), brain injury following ischemia (Arvin, B., et al., *Ann. NY Acad. Sci.,* 1995, 765, 62–71), non-insulin-dependent diabetes mellitus (Hotamisligil, G. S., et al., *Science,* 1993, 259, 87–90), insulin-dependent diabetes mellitus (Yang, X. -D., et al., *J. Exp. Med.,* 1994, 180, 995–1004), hepatitis (Ksontini, R., et al., *J. Immunol.,* 1998, 160, 4082–4089), atopic dermatitis (Sumimoto, S., et al., *Arch. Dis. Child.,* 1992, 67, 277–279), and pancreatitis (Norman, J. G., et al., *Surgery,* 1996, 120, 515–521). Further, Suganuma, M., et al. (*Cancer Res.,* 1996, 56, 3711–3715) suggest that inhibitors of TNF-α may be useful for cancer prevention. In addition, elevated TNF-α expression may play a role in obesity (Kern, P. A., *J. Nutr.,* 1997, 127, 1917S–1922S). TNF-α was found to be expressed in human adipocytes and increased expression, in general, correlated with obesity.

Two major classes of drugs have been used to induce differentiation. Retinoic acids are used for the treatment of various leukemias (Chomienne, C., et al., *FASEB J.,* 1996, 10, 1025–1030) and skin disorders (Orfanos, C. E., et al., *Drugs,* 1997, 53, 358–388). A major side effect of retinoic acids in their teratogenicity. Vitamin D3 derivatives are currently being studied for use in skin disorders (Gniadecki, R., *Br. J. Pharmacol.,* 1997, 120, 1119–1127; Kobayashi, T., *J. Dermatol. Sci.,* 1998, 16, 158–164).

Although numerous compounds have been identified as PKC inhibitors (see Hidaka and Hagiwara, *Trends in Pharm. Sci.,* 1987, 8, 162–164 for review), few have been found which inhibit PKC specifically, much less specific isozymes of PKC. While the quinoline sulfonamide derivatives such as 1-(5-isoquinolinesulfonyl)-2-methylpiperazine (H-7) inhibit PKC at micromolar concentrations, they exhibit similar enzyme inhibition kinetics for PKC and the cAMP-dependent and cGMP-dependent protein kinases. Staurosporine, an alkaloid product of Streptomyces sp., and its analogs, are the most potent in vitro inhibitors of PKC identified to date. However, they exhibit only limited selectivity among different protein kinases (Gescher, *Anti-Cancer Drug Design,* 1989, 4, 93–105). Certain ceramides and sphingosine derivatives have been shown to have PKC inhibitory activity and to have promise for therapeutic uses, however, there remains a long-felt need for specific inhibitors of the enzymes.

There is also a desire to inhibit specific PKC isozymes, both as a research tool and in diagnosis and treatment of diseases which may be associated with particular isozymes. It is presently believed that different PKC isozymes may be involved in various disease processes depending on the organ or tissue in which they are expressed. Thus far, PKC isozyme specific antisense oligonucleotides have been used to study PKC-α (McGraw, K., et al., *Anti-Cancer Drug Des.,* 1997, 12, 315–326), and an antisense oligonucleotide drug, ISIS 3521, targeted to PKC-α is presently in clinical trials and has demonstrated encouraging results in patients with solid tumours. Antisense oligonucleotides have also been used to inhibit PKC-β (Gamard, C. J., *Cell Growth Diff.,* 1994, 5, 405–409), PKC-ε (Traub, O., et al., *J. Biol. Chem.,* 1997, 272, 31251–31257), and PKC-ζ (Liao, D. F., *J. Biol. Chem.,* 1997, 272, 6146–6150). Diaz-Meco Conde et al. disclose a peptide corresponding to the pseudo-substrate region of PKC-ζ and oligonucleotides antisense to this isozyme (WO Application 93/20101). Alvaro et al. have identified a novel mutant form of PKC associated with tumors and disclose oligonucleotide sequences complementary to the mutant form (WO Application 94/29455).

Specific inhibitors of PKC-δ are believed to be useful for studying the precise role of this isozyme and for therapeutic applications. A compound isolated from *Mallotus philippinensis,* rotterlin, shows some specificity to PKC-δ relative to other PKC family members (Gschwendt, M., et al., *Biochem. Biophys. Res. Commun.,* 1994, 199, 93–98). However, this compound also shows some inhibition of other protein kinases including calmodulin-dependent protein kinase III.

Antisense oligonucleotides specific for the PKC-δ isozyme have also been used. Liedtke, C. M., et al. (*Am. J. Physiol.,* 1997, 273, C1632–C1640) used an oligonucleotide complementary to the translation initiation region of mouse PKC-δ to block $α_1$-adrenergic activation of Na-K-2Cl cotransport. Pessino, A., et al. (*Biochem. J.,* 1995, 312, 549–554) used an oligonucleotide complementary to the translation initiation region of PKC-δ to decrease PKC-δ levels and induce differentiation of murine erythroleukemia cells.

There are currently several approaches for directly inhibiting TNF-α expression. These include antibodies, human soluble TNF-α receptor (Camussi, G., *Drugs,* 1998, 55, 613–620) and oligonucleotides, including triplex-forming oligonucleotides, ribozymes, and antisense oligonucleotides. Examples of indirect TNF-α inhibitors include phosphodiesterase inhibitors (e.g. pentoxifylline) and metalloprotease inhibitors (Eigler, A., et al., *Immunol. Today,* 1997, 18, 487–492). Indirect inhibitors of TNF-α, such as an inhibitor in the TNF-α signaling pathway, may provide means to inhibit a broad spectrum of activities associated with immune and inflammatory diseases.

There remains a long-felt need for improved compositions and methods for inhibiting PKC-δ gene expression.

SUMMARY OF THE INVENTION

The present invention provides oligonucleotides which are targeted to nucleic acids encoding human PKC-δ and are capable of inhibiting PKC-δ expression. The present invention also provides chimeric oligonucleotides targeted to nucleic acids encoding human PKC-δ. The oligonucleotides of the invention are believed to be useful both diagnostically and therapeutically, and are believed to be particularly useful in the methods of the present invention.

The present invention also comprises methods of inhibiting the expression of human PKC-δ. These methods are believed to be useful both therapeutically and diagnostically as a consequence of the association between PKC-δ inhibition and differentiation and signal transduction leading to TNF-α expression. These methods are also useful as tools, for example, for detecting and determining the role of PKC-δ expression in various cell functions and physiological processes and conditions and for diagnosing conditions associated with PKC-δ or TNF-α expression.

The present invention also comprises methods of modulating differentiation or cell signaling in cells using oligonucleotides of the invention. These methods are believed to be useful, for example, in diagnosing PKC-δ-associated cell differentiation and diseases or conditions associated with TNF-α expression. Methods of treating abnormal differentiation conditions or inflammatory and immune diseases or conditions are also provided. These methods employ the oligonucleotides of the invention. These methods are believed to be useful both therapeutically and as clinical research and diagnostic tools.

DETAILED DESCRIPTION OF THE INVENTION

Many diseases are associated with unregulated control of cellular differentiation or TNF-α-associated cell signaling.

Examples of diseases associated with unregulated control of cellular differentiation include leukemias and skin disorders such as psoriasis. Examples of diseases associated with TNF-α include infectious and inflammatory diseases, particularly diabetes, rheumatoid arthritis, Crohn's disease, pancreatitis, multiple sclerosis, atopic dermatitis and hepatitis. A method of treatment for these diseases could include induction of cellular differentiation or modulation of TNF-α associated cell signaling. The PKC family members are important regulators of cellular proliferation and differentiation. Targeting individual isozymes of PKC could be a useful method to control diseases associated with unregulated cellular differentiation or cell signaling.

Certain abnormal conditions associated with unregulated control of differentiation or cell signaling are believed to be associated with PKC-δ expression and are, therefore believed to be responsive to inhibition of PKC-δ expression.

The relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence shows function is to be modulated. This may be, as examples, a cellular gene (or mRNA made from the gene) whose expression is associated with a particular disease state, or a foreign nucleic acid from an infectious agent. In the present invention, the target is a nucleic acid encoding PKC-δ; in other words, a gene encoding PKC-δ, or mRNA expressed from the PKC-δ gene. mRNA which encodes PKC-δ is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo or initiate translation of an mRNA molecule transcribed from a gene encoding PKC-δ, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanoside residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compound targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytoside are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment and, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of PKC-δ and, in the context of this invention, ultimately modulation of cellular adhesion molecule expression. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently a preferred form of modulation.

The oligonucleotides of this invention can be used in diagnostics, therapeutics, prophylaxis, and as research reagents and in kits. Since the oligonucleotides of this invention hybridize to nucleic acids encoding PKC-δ, sandwich, colorimetric and other assays can easily be constructed to exploit this fact. Provision of means for detecting hybridization of oligonucleotide with the PKC-δ gene or mRNA can routinely be accomplished. Such provision may include enzyme conjugation, radiolabelling or any other suitable detection systems. Kits for detecting the presence or absence of PKC-δ may also be prepared.

The present invention is also suitable for diagnosing abnormal inflammatory states in tissue or other samples from patients suspected of having an inflammatory disease such as rheumatoid arthritis. The ability of the oligonucleotides of the present invention to inhibit inflammatory processes may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotdes means to add the oligonucleotide (s), usually in a liquid carrier, to a cell suspension or tissue sample, either in vitro or ex vivo, or to administer the oligonucleotide(s) to cells or tissues within an animal.

The oligonucleotides of this invention may also be used for research purposes. For example, the function of a specific gene product in a signaling pathway may be investigated using specific oligonucleotides. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleotides that include a pentofuransyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithiolates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionohosphoramidates, thionoalkylphosphonates, thionoalkylphosphotriesters, and borano-phosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. No. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbone; sulfide, sulfoxide and sulfone backbones; formacetyl and thioformacetyl backbones; methylene formacetyl and thioformacetyl backbones; alkene containing backbones; sulfamate backbones; methleneimino and methenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. No. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amido portion of the backbone. Representative United States patents that teach the preparation of PNA compounds include, but are not limited to, U.S. Pat. No. 5,539,082; 5,714,331; and 5,719,262. Further teaching of PNA compounds can be found in Nielsen et al. (*Science*, 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —$CH_2$—N($CH$)$_3$—O—CH—$_2$ [known as a methylene (methylimino) or MMI backbone], —$CH_2$—O—N($CH_3$)—$CH_2$—, —$CH_2$—N($CH_3$)—N($CH_3$)—$CH_2$— and —O—N($CH$)$_3$—$CH$—$_2CH$—$_2$ [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl, O-alkyl-O-alkyl, O-, S-, or N-alkenyl, or O-, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_m$ $CH_3$, $O(CH_2)_nOCH_3$, $O(CH_2)_2ON(CH_3)_2$, $O(CH_2)_nNH_2$, $O(CH_2)_nCH_3$, $O(CH_2)_nONH_2$, and $O(CH_2)_nON[(CH_2)_n CH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy 2'—O—$CH_2CH_2OCH_3$, also known as 2'—O—(2-methoxyethyl) or 2'-MOE) (Martin et al., *Helv. Chim. Acta* 1995, 78, 486–504) i.e., an alkoxyalkoxy group. Further preferred modifications include 2'-dimethylaminooxyethoxy, i.e., a $O(CH_2)_2ON(CH_3)_2$ group, also known as 2'-DMAOE, and 2'-dimethylaminoethoxyethoxy (2'-DMAEOE) as described in examples hereinbelow.

Other preferred modifications include 2'-methoxy (2'—O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. No. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pages 858–859, Kroschwitz, J. I., ed. John Wiley & Sons, those disclosed by Englisch et al. (*Angewandte Chemie, International Edition* 1991, 30, 613–722), and those disclosed by Sanghvi, Y. S., Chapter 15, *Antisense Research and Applications* 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. U.S.A.* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. Pharmacol. Exp. Ther.*, 1996, 277, 923–937).

Representative United States patents that teach the preparation of such oligonucleotide conjugates include, but are not limited to, U.S. Pat. No. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An addition region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'—O—CH$_2$CH$_2$OCH$_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—CH$_2$CH$_2$OCH$_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modification, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., *Helv. Chim. Acta* 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermindine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention.

Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651–654).

The physiological roles of bile include the facilitation of dispersion and absorption of lipids and fat-soluble vitamins (Brunton, Chapter 38 In: *Goodman & Gilman's The Pharmacological Basis of Therapeutics,* 9th Ed. Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al, *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier*

Systems 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of the present invention, such as dyes, flavoring agents, preservatives, antioxidants, opacifiers, thickening agents and stabilizers. However, such materials, when added, should no unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, blemoycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, *The Merck Manual of Diagnosis and Therapy*, 15th Ed. 1987, pp. 1206–1288, Berkow et al., eds. Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}s$ found to be effective in vitro and in in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

Thus, in the context of this invention, by "therapeutically effective amount" is meant the amount of the compound which is required to have a therapeutic effect on the treated individual. This amount, which will be apparent to the skilled artisan, will depend upon the age and weight of the individual, the type of disease to be treated, perhaps even the gender of the individual, and other factors which are routinely taken into consideration when designing a drug treatment. A therapeutic effect is assessed in the individual by measuring the effect of the compound on the disease state in the animal. For example, if the disease to be treated is cancer, therapeutic effects are assessed by measuring the rate of growth or the size of the tumor, or by measuring the production of compounds such cytokines, production of which is an indication of the progress of regression of the tumor.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.)

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc. Sterling, Va.

2'-fluoro oligonucleotides are synthesized as described in Kawasaki et al. (J. Med. Chem. 1993, 36, 831–841). Briefly, the protected nucloeside $N^6$-benzoyl-2'-deoxy-2'-fluoroadenosine is synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine is selectively protected in moderate yield as the 3', 5'-ditetrahydropyranyl (THP) intermediate. Deprotection of the THP and $N^6$-benzoyl groups is accomplished using standard methodologies and standard methods are used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'-phosphoramidites.

2'-deoxy-2'-fluorocytidine is synthesized via amination of 2'-deoxy-2'-fluorouridine, followed by selective protection to give $N^4$-benzoyl-2'-deoxy-2'-fluorocytidine. Standard procedures are used to obtain the 5'-DMT and 5'-DMT-3'-phosphoramidites.

2'-(2-methoxyethyl)-modified amidites were synthesized according to Martin, P. (Helv. Chim. Acta 1995, 78, 486–506). For ease of synthesis, the last nucleotide may be a deoxynucleotide. 2'—O—$CH_2CH_2OCH_3$-cytosines may be 5-methyl cytosines.

Synthesis of 5-Methyl cytosine monomers:

2,2'-Anhydro[1-(β-D-arabinofuranosyl)-5-methyluridine]:

5-Methyluridine (ribosylthymine, commercially available through Yamasa, Chosi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h). to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$Cl$_2$/acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/Hexane/Acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2-2'-O-methoxyethyl-5'-O-dimethoxytrityl-5-methyluridine:

2'-O-Methoxyethyl-5'-O-dimethoxytrityl-5-methyluridine (106 g, 0.167 M), DMF/pyridine (750 mL of a 3:1 mixture prepared form 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane (4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the alter solution. The resulting reaction mixture was stored overnight in a cold room Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite:

N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washed were back-extracted with CH$_2$Cl$_2$ (300 mL), and the extracts were combined, dried over MgSO$_4$ and concentrated. The residue obtained was chromatographed on a 1.5 kg silica column using EtOAc/Hexane (3:1) as the eluting solvent. The pure fractions were combined to give 90.6 g (87%) of the title compound. 5-methyl-2'-deoxycytidine (5-me-C) containing oligonucleotides were synthesized according to published methods (Sanghvi et al., *Nucl. Acids Res.* 1993, 21, 3197–3203) using commercially available phosphoramidites (Glen Research, Sterling Va. or ChemGenes, Needham Mass.).

2'-O-(dimethylaminooxyethyl) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O-$^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The produce will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle ) was added to get a clear solution. Diethylazodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. After 1 hr the mixture was filtered, the filtrate was washed with ice cold $CH_2Cl_2$ and the combined organic phase was washed with water, brine and dried over anhydrous $Na_2 SO_4$. The solution was concentrated to get 2'-O-(aminooxyethyl) thymidine, which was then dissolved in MeOH 67.5 mL. To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy)ethyl]-5-methyluridine as white foam (1.95, 78%).

5'-O-tert-Butyldiphenylsilyl-2'-O-[N,N-dimethylaminooxyethyl]-5-methyluridine

5'-O-tert-butyldiphenylsilyl-2'O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2 SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$. Solvent was removed under vacuum and the residue placed on a flash column and eluted with 10% MeOH in $CH_2Cl_2$to get 2'-O-(dimethylaminooxyethyl)-5-methyluridine (766 mg, 92.5%).

5'-O-DMT-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the reside chromatographed and eluted with 10% MeOH in $CH_2Cl_2$ (containing a few drops of pyridine) to get 5'-O-DMT-2'-O-(dimethylamino-oxyethyl-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL), 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N,-diisopropylphosphoramidite] as a foam (1.04 g, 74.9%).

2'-dimethylaminoethoxyethoxy (2'-DMAEOE) nucleoside amidites

2'-dimethylaminoethoxyethoxy (2'-DMAEOE) nucleoside amidites (also known in the art as 2'-O-dimethylaminoethoxyethyl) or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using $MeOH:CH_2Cl_2:Et_3N$ (20:1, v/v, with 1% triethylamine) gives the title compound.

5'-O-Dimethoxytrityl-2'-O-[2(2-N,N-dimethylaminoethoxy)ethoxy)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages were synthesized and incorporated into oligonucleotides. Other nitrogen-containing backbones are synthesized according to WO 92/20823 which is also coassigned to the assignee of the present invention and incorporated therein in its entirety.

Oligonucleotides having amide backbones are synthesized according to De Mesmaeker et al. (*Acc. Chem. Res.* 1995, 28 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (*Science* 1991, 254, 1497–1500).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

Example 2

Design and Testing of Human PKC-δ Oligonucleotide Sequences for Inhibition of PKC-δ mRNA Antisense oligonucleotides targeted to human PKC-δ were designed and synthesized as phosphorothioate oligodeoxynucleotides according to Example 1; oligonucleotide sequences are presented in Table 1. PKC-δ sequence data are from the cDNA sequence published by Aris et al. (*Biochim. Biophys. Acta,* 1993, 1174, 171–181); Genbank accession number L07860. This sequence is provided herein as SEQ ID NO: 1.

TABLE 1

Oligonucleotide Sequences Targeted to Human PKC-δ

| ISIS NO. | NUCLEOTIDE SEQUENCE[1] (5'→3') | SEQ ID NO: | TARGET GENE NUCLEOTIDE CO-ORDINATES[2] | GENE TARGET REGION | % mRNA INHIBITION |
|---|---|---|---|---|---|
| 10299 | GCAGGAACGGCGCCATGGTG | 3 | 0055–0074 | AUG | — |
| 10300 | CTGGTTCGCCTCGTCCTCGG | 4 | 0114–0133 | ORF | 28 |
| 10301 | ATCTGGATGACGCGCCCCTC | 5 | 0251–0270 | ORF | 30 |
| 10302 | TTCTTGCAGCGCTCGGCCAG | 6 | 0329–0348 | ORF | 9 |
| 10303 | TGCAATCCACGTCCTCCAGG | 7 | 0421–0440 | ORF | 47 |
| 10304 | AAGCGGTGCGGCATGTCGAT | 8 | 0480–0499 | ORF | 13 |
| 10305 | AAGCGGTGCGGCATGTCGAT | 9 | 0737–0756 | ORF | 41 |
| 10306 | GCAGGCTGCCGCAGTGGTCA | 10 | 0790–0809 | ORF | 13 |
| 10307 | CCTCCCCAGCAACTCCGGTC | 11 | 1015–1034 | ORF | 36 |
| 10308 | AGCGGCCTTTGTCCTGGATG | 12 | 1372–1391 | ORF | 10 |
| 10309 | GGCCATCCCGGTCCAACAGC | 13 | 1495–1514 | ORF | 42 |
| 10310 | GGTGCTGGCCCGGCTCTCCC | 14 | 1560–1579 | ORF | 62 |
| 10311 | GGACCCCGAAAGACCACCAG | 15 | 1648–1667 | ORF | 72 |
| 10312 | GTGGCTCCAACCTCCGCTTT | 16 | 1894–1913 | ORF | 21 |
| 10313 | AGGAGGTGCTCGAATTTGGG | 17 | 2060–2079 | ORF | — |

[1]All linkages are phosphorothioate linkages.
[2]Co-ordinates from Genbank Accession No. L07860, locus name "HUMPCKD13X", SEQ ID NO. 1.

A549 cells (obtained from the American Type Culture Collection) were routinely passaged at 80–90% confluency in Dulbecco's modified Eagle's medium (DMEM) containing 1 g glucose/liter and 10% fetal bovine serum (Hyclone, Logan Utah).

A549 cells were treated with phosphorothioate oligonucleotides at 400 nM for four hours in the presence of the cationic lipids DOTMA/DOPE, washed and allowed to recover for an additional 20 hours. Total RNA was extracted and 15 μg of each was resolved on 1% gels and transferred to nylon membranes. The blots were probed with a $^{32}$P radiolabeled PKC-δ cDNA probe and then stripped and reprobed with a radiolabeled G3PDH probe to confirm equal RNA loading. The PKC-δ cDNA probe consisted of a 2.1 kb NheI fragment from pBlueBAC-PKC-δ (American Type Culture Collection, Manassas, Va.). The glyceraldehyde 3-phosphate dehydrogenase (G3PDH) probe was purchased from Clontech (Palo Alto, Calif.), Catalog Number 9805-1. PKC-δ transcripts were examined and quantified with a PhosphorImager (Molecular Dynamics, Sunnyvale, Calif.). Results are shown in Table 1 as percent mRNA inhibition compared to control (untreated). Oligonucleotides 10303 (SEQ ID NO: 7), 10305 (SEQ ID NO: 9), 10309 (SEQ ID NO: 13), 10310 (SEQ ID NO: 14) and 10311 (SEQ ID NO: 15) gave better than 40% reduction of PKC-δ mRNA levels. Oligonucleotides 10310 and 10311 gave better than 60% reduction of PKC-δ.

Example 3

Dose Response of Chimeric (deoxy gapped) 2'-O-methoxyethyl PKC-δ Antisense Oligonucleotides on PKC-δ mRNA Levels in NHEK Cells SEQ ID NO: 15 was synthesized as a uniformly phosphorothioate chimeric oligonucleotide having a centered deoxy gap of eight nucleotides flanked by 2'-O-methoxyethyl (2'-MOE) regions. All 2'-MOE cytosines were 5-me-cytosines. An additional chimeric oligonucleotide (SEQ ID NO: 18) was synthesized having a randomized sequence and identical base composition for use as a "scrambled" control.

TABLE 2

Nucleotide Sequences of Chemically-modified Human PKC-δ Phosphorothioate Oligonucleotides

| ISIS NO. | NUCLEOTIDE SEQUENCE[1] (5'→3') | SEQ ID NO: | TARGET GENE NUCLEOTIDE CO-ORDINATES[2] | GENE TARGET REGION |
|---|---|---|---|---|
| 10311 | GGACCCCGAAAGACCACCAG | 15 | 1648–1667 | ORF |
| 13513 | GGACCCCGAAAGACCACCAG | 15 | 1648–1667 | ORF |
| 17252 | GGACCCCGAAAGACCACCAG | 15 | 1648–1667 | ORF |
| 13514 | AGCCCACCGAGACACCGAGA | 18 | scrambled control | 13513 |

[1]Emboldened residues are 2'-O-methoxyethyl- residues (others are 2'-deoxy-). All 2'-O-methoxyethyl-cytosines are 5-methyl-cytosines; all linkages are phosphorothioate linkages.
[2]Co-ordinates from Genbank Accession No. L07860, locus name "HUMPCKD13X", SEQ ID NO. 1.

NHEK (Normal human epidermal keratinocyte) cells (Clonetics, San Diego Calif.) were grown in Keratinocyte Growth Medium (KGM) (Gibco BRL, Gaithersburg, Md.) containing 5 ng/ml of EGF, bovine pituitary extract. NHEK were used at passages 3–5.

NHEK were grown to 60–80% confluency, washed once with basal medium, and then incubated for 4 hours with 5 ml of basal medium containing 10 μg/ml LIPOFECTIN™ (Gibco BRL, Gaithersburg, Md.) and the indicated concentration of oligonucleotide. mRNA was processed and quantified as described in Example 2.

Oligonucleotides 13513 (SEQ ID NO. 15) and 13514 (SEQ ID NO. 18) were tested at various concentrations. Results are shown in Table 3. Oligonucleotide 13513 (SEQ ID NO. 15) gave approximately 85% inhibition at 300 nM concentration. The $IC_{50}$ is approximately 150 nM. Minimal inhibition was seen with control oligonucleotide 13514 (SEQ ID NO. 18).

TABLE 3

Dose Response of A549 Cells to PKC-δ Antisense Oligonucleotides (ASOs)

| ISIS # | SEQ ID NO: | ASO Gene Target | Dose | % mRMA Inhibition |
|---|---|---|---|---|
| control | — | LIPOFECTIN ™ only | — | 0% |
| 13513 | 15 | ORF | 50 nM | 10% |
| 13513 | 15 | " | 100 nM | 35% |
| 13513 | 15 | " | 200 nM | 60% |
| 13513 | 15 | " | 300 nM | 85% |
| 13514 | 18 | scrambled | 50 nM | 5% |
| 13514 | 18 | " | 100 nM | 10% |
| 13514 | 18 | " | 200 nM | 5% |
| 13514 | 18 | " | 300 nM | 10% |

Example 4

Time Course of Chimeric Antisense Oligonucleotides on PKC-δ Protein Levels in NHEK Cells NHEK cells were cultured and treated with oligonucleotide as described in Example 3. Oligonucleotide concentration was 300 nM.

Immunoblot assay:

Cell extracts were electrophoresed on 10% SDS-PAGE mini-gels. The resolved proteins were transferred to Immobilon-P membrane (Millipore, Bedford Mass.) by electrophoretic transfer and the membrane was blocked for 60 minutes in TBS (Tris-HCl pH 7.4, 150 mM NaCl) containing 5% nonfat milk. The membrane was then incubated for 16 hours at 4° C. with monoclonal antibodies raised against PKC-δ (Santa Cruz Biotechnology, Santa Cruz Calif.) diluted to 0.2 μg/ml in TBS containing 0.2% nonfat milk. This was followed by three washes in TBS plus 0.2% nonfat milk. The membrane was then incubated for one hour with $^{125}$I-labelled goat anti-mouse secondary antibody (ICN Radiochemicals, Irvine Calif.). Membranes were then washed extensively in TBS plus 0.2% nonfat milk. Bands were visualized and quantitated using a Phosphorimager (Molecular Dynamics, Sunnyvale, Calif.). Results are shown in Table 4. Oligonucleotide 13513 (SEQ ID NO. 15) gave greater 85% inhibition after 120 hours. Minimal inhibition was seen with oligonucleotide 13514 (SEQ ID NO. 18).

TABLE 4

Time Course of Response of Cells to Human PKC-δ Antisense Oligonucleotides (ASOs)

| ISIS # | SEQ ID NO: | ASO Gene Target Region | Time | % Protein Inhibition |
|---|---|---|---|---|
| basal | — | LIPOFECTIN ™ only | 24 h | 0% |
| basal | — | " | 48 h | 0% |
| basal | — | " | 72 h | 0% |
| basal | — | " | 96 h | 0% |
| basal | — | " | 120 h | 0% |
| 13513 | 15 | ORF | 24 h | 20% |
| 13513 | 15 | " | 48 h | 40% |
| 13513 | 15 | " | 72 h | 70% |
| 13513 | 15 | " | 96 h | 80% |
| 13513 | 15 | " | 120 h | 85% |
| 13514 | 18 | scrambled | 24 h | 5% |
| 13514 | 18 | " | 48 h | — |
| 13514 | 18 | " | 72 h | 9% |
| 13514 | 18 | " | 96 h | 10% |
| 13514 | 18 | " | 120 h | 20% |

Example 5

Specificity of Chimeric Antisense Oligonucleotides to PKC-δ

The specificity of PKC-δ antisense oligonucleotides was determined by measuring mRNA levels, as described in Example 3, and protein levels, as described in Example 4. mRNA expression levels of PKC-δ, η and ζ were determined 24 hours after treatment. Protein levels of PKC-d, m and ζ were determined 72 hours after oligonucleotide treatment. Only PKC-δ expression was inhibited by oligonucleotide 13513 (SEQ ID NO. 15), demonstrating the specificity of the oligonucleotide.

Example 6

Effect of PKC-δ Inhibition on TPA Responsive Genes

Many genes, including late stage markers of differentiation and multiple matrix metalloproteinases, are regulated by TPA. The matrix metalloproteinases (MMPs) are a family of enzymes which have the ability to degrade components of the extracellular matrix (Birkedal-Hansen, *Current Op. Biol.* 7:728 (1995)). Many members of the MMP family have been found to have elevated levels of activity in human tumors as well as other disease states (Stetler-Stevenson et al., *Annu. Rev. Cell Biol.* 9:541 (1993); Bernhard et al., *Proc. Natl. Acad. Sci. (U.S.A.)* 91:4293 (1994)). The following genes were examined for their ability to be induced by the phorbol ester TPA (12-O-tetradecanoylphorbol 13-acetate) and the ability of antisense oligonucleotides targeted to PKC-δ to block this induction: involucrin, keratinocyte transglutaminase, filiggrin, and the matrix metalloproteinases, MMP-1 (interstitial collagenase) and MMP-9 (92 kd gelatinase B). Only induction of MMP-1 expression was inhibited by PKC-δ antisense oligonucleotides; inhibition was >90%.

Example 7

Inhibition of TNF-α Expression by Antisense Inhibition of PKC-δ

NHEK (Normal human epidermal keratinocyte) cells (Clonetics, San Diego Calif.) were grown in Keratinocyte Growth Medium (KGM) (Gibco BRL, Gaithersburg Md.) containing 5 ng/ml of EGF, bovine pituitary extract. NHEK cells were used at passage 4.

NHEK were grown to 60–80% confluency, washed once with basal medium, and then incubated for 4 hours with basal medium containing 6 µg/ml LIPOFECTIN™ (Gibco BRL, Gaithersburg Md.) and 200 nM oligonucleotide. Following oligonucleotide treatment, the media was replaced with growth medium and the cells allowed to recover approximately 24 hours. A second oligonucleotide treatment was performed for 5 hours in the presence of LIPOFECTIN™. After 48 hours post-treatment, the medium was removed and the cells were further incubated in Keratinocyte medium containing the supplied growth factors and 100 nM phorbol 12-myristate 13-acetate (PMA, Sigma, St. Louis, Mo.). mRNA was analyzed 2 hours post-induction with PMA. Protein levels were analyzed approximately 12 hours post-induction.

Total mRNA was isolated using the RNEASY® Mini Kit (Qiagen, Valencia, Calif.; similar kits from other manufacturers may also be used), separated on a 1% agarose gel, transferred to HYBOND™-N+ membrane (Amersham Pharmacia Biotech, Piscataway, N.J.), a positively charged nylon membrane, and probed. A TNF-α probe consisted of the 505 bp EcoRi-HindIII fragment from BBG 18 (R&D Systems, Minneapolis, Minn.), a plasmid containing human TNF-α cDNA.

A glyceraldehyde 3-phosphate dehydrogenase (G3PDH) probe consisted of the 1.06 kb HindIII fragment from pHcGAP (American Type Culture Collection, Manassas, Va.), a plasmid containing human G3PDH cDNA. The restriction fragments were purified from low-melting temperature agarose, as described in Maniatis, T., et al., *Molecular Cloning: A Laboratory Manual,* 1989 and labeled with REDIVUE™ $^{32}$P-dCTP (Amersham Pharmacia Biotech, Piscataway, N.J.) and PRIME-A-GENE® labelling kit (Promega, Madison, Wis.). mRNA was quantitated by a PhosphoImager (Molecular Dynamics, Sunnyvale, Calif.).

Secreted TNF-α protein levels were measured using a human TNF-α ELISA kit (R&D Systems, Minneapolis, Minn. or Genzyme, Cambridge, Mass.).

Results are shown in Table 5. ISIS 17252 (SEQ ID NO. 15) was able to reduce TNF-α mRNA expression by approximately 50% and TNF-α protein secretion by approximately 90%. Antisense oligonuclectides to other PKC isoforms including α, ε, and ξ did not reduce TNF-α mRNA or protein levels.

TABLE 5

Inhibition of TNF-α mRNA expression and TNF-α protein secretion by a PKC-δ antisense oligonucleotide

| ISIS No: | SEQ ID NO: | GENE TARGET REGION | % mRNA EXPRESSION | % PROTEIN SECRETION |
|---|---|---|---|---|
| basal | — | — | 1% | 0% |
| induced | — | — | 100% | 100% |
| 17252 | 15 | ORF | 54% | 12% |

Example 8

Effect of Antisense Inhibitors of TNF-α in a Murine Model for Non-Insulin-dependent Diabetes Mellitus The db/db mouse model, a standard model for non-insulin-dependent diabetes mellitus (NIDDM; Hotamisligil, G. S., et al., *Science,* 1993, 259, 87–90), was used to assess the activity of TNF-α antisense oligonucleotides on blood glucose levels and TNF-α mRNA levels in whole mice. These mice have elevated blood glucose levels and TNF-α mRNA levels compared to wild type mice. Female db/db mice and wild-type littermates were purchased from Jackson Laboratories (Bar Rarbor, Me.). The effect on oligonucleotide 15931 (SEQ ID NO. 19) on blood glucose levels was determined. For determination of TNF-α mRNA levels, oligonucleotide 15931 (SEQ ID NO. 19), a uniformly modified phosphorothioate oligodeoxynucleotide, was compared to oligonucleotide 25302 (SEQ ID NO. 19), a mixed phosphorothioate/phosphodiester chimeric oligonucleotide having regions of 2'-O-methoxyethyl (2'-MOE) nucleotides and deoxynucleotides. The sequences and chemistries are shown in Table 6. Oligonucleotide 18154 (SEQ ID NO. 20) is an antisense mixed phosphorothioate/phosphodiester chimeric oligonucleotide, having regions of 2'-O-methoxyethyl (2'-MOE) nucleotides and deoxynucleotides, targeted to the human vascular cell adhesion molecule-1 (VCAM-1) and was used as an unrelated target control.

TABLE 6

Nucleotide Sequence of TNF-α Antisense Oligonucleotides

| ISIS NO. | NUCLEOTIDE SEQUENCE[1] (5'→3') | SEQ ID NO: | TARGET GENE NUCLEOTIDE CO-ORDINATES[2] | GENE TARGET REGION |
|---|---|---|---|---|
| 15931 | AACCCATCGGCTGGCACCAC | 19 | 5891–5910 | coding |
| 25302 | AACCCATCGGCTGGCACCAC | 19 | 5891–5910 | coding |
| 18154 | TCAAGCAGTGCCACCGATCC | 20 | target control | |

[1]Emboldened residues are 2'-methoxyethyl residues. All 2'-methoxyethyl cytosines and 2'-deoxy cytosines residues are 5-methyl-cytosines; all linkages are phosphorothioate linkages.
[2]Co-ordinates from Genbank Accession No. Y00467, locus name "MMTNFAB".

db/db mice, six to ten weeks old, were dosed intraperitoneally with oligonucleotide every other day for 2 weeks at 10 mg/kg. The mice were fasted for seven hours prior to administration of the oligonucleotide. The mice were bled via retro orbital sinus every other day, and glucose measurements were performed on the blood. Results are shown in Table 7. Oligonucleotide 15931 (SEQ ID NO. 19) was able to reduce blood glucose levels in db/db mice to levels comparable with wild type mice. Food intake between wild type mice, treated and untreated, did not differ. Food intake between db/db mice, treated and untreated, although higher than wild type mice, did not differ significantly.

Samples of the fat (adipose) tissue from the inguinal fat pads were taken for RNA extraction. RNA was extracted according to Current Protocols in Molecular Biology, 1997, Ausubel, F., et al. ed., John Wiley & Sons. RNA was purified using the RNA clean up procedure of the RNEASY® Mini kit (Qiagen, Valencia, Calif.). TNF-α mRNA levels were measured using the RIBOQUANT® kit (PharMingen, San Diego, Calif.) with 15 µg of RNA per lane. The probe used was from the mCK-3b Multi-Probe Template set (PharMingen, San Diego, Calif.) labelled with [α$^{32}$P]UTP (Amersham Pharmacia Biotech, Piscataway, N.J.). Results are shown in Table 8. Both oligonucleotide 15931 (SEQ ID NO. 19) and 25302 (SEQ ID NO. 19) were able to reduce TNF-α levels in fat, with 25302 (SEQ ID NO. 19) reducing TNF-α to nearly wild-type levels.

Inhibition of TNF-α has been shown to be effective in a non-insulin diabetes mellitus model.

TABLE 7

Level of Blood Glucose in Normal and db/db Mice After Treatment with TNF-α Antisense Oligonucleotides

| Mouse Strain | ISIS # | SEQ ID NO: | ASO Gene Target | Time (days) | blood glucose (mg/dL) |
|---|---|---|---|---|---|
| wild type | — | — | — | 1 | 140 |
| " | 15931 | 19 | coding | " | 138 |
| db/db | — | — | — | 1 | 260 |
| " | 15931 | 19 | coding | " | 254 |
| wild type | — | — | — | 9 | 175 |
| " | 15931 | 19 | coding | " | 163 |
| db/db | — | — | — | 9 | 252 |
| " | 15931 | 19 | coding | " | 128 |

TABLE 8

Level of TNF-α mRNA in Fat of db/db Mice after Treatment with TNF-α Antisense Olignonucleotides

| ISIS No: | SEQ ID NO: | GENE TARGET REGION | % mRNA EXPRES-SION |
|---|---|---|---|
| wt saline | — | — | 100% |
| db/db saline | — | — | 362% |
| 18154 | 20 | control | 130% |
| 15931 | 19 | coding | 210% |
| 25302 | 19 | coding | 417% |

Example 9

Effect of Antisense Inhibition of TNF-α in a Murine Model for Rheumatoid Arthritis Collagen-induced arthritis (CIA) was used as a murine model for arthritis (Mussener, A., et al., Clin. Exp. Immunol., 1997, 107, 485–493). Female DBA/1LacJ mice (Jackson Laboratories, Bar Harbor, Me.) between the ages of 6 and 8 weeks were used to assess the activity of TNF-α antisense oligonucleotides.

On day 0, the mice were immunized at the base of the tail with 100 µg of bovine type II collagen which is emulsified in Complete Freund's Adjuvant (CFA). On day 7, a second booster dose of collagen was administered by the same route. On day 14, the mice were injected subcutaneously with 100 µg of LPS. Oligonucleotide was administered intraperitoneally daily (10 mg/kg bolus) starting on day −3 three days before day 0) and continuing for the duration of the study.

Weights were recorded weekly. Mice were inspected daily for the onset of CIA. Paw widths are rear ankle widths of affected and unaffected joints were measured three times a week using a constant tension caliper. Limbs were clinically evaluated and graded on a scale from 0–4 (with 4 being the highest).

Oligonucleotide 25302 (SEQ ID NO. 19) was compared to a saline control. The antisense TNF-α oligonucleotide reduced the incidence of CIA from 70% for the saline control to 40% for the oligonucleotide. The severity of the disease (based on the mean score of the limbs) was also reduced from 3.2 for the saline control to 2.1 for the oligonucleotide.

Inhibition of TNF-α has been shown to be effective in a rheumatoid arthritis model.

Example 10

Effect of Antisense Inhibition of TNF-α in a Murine Model for Contact Sensitivity Contact sensitivity is a type of immune response resulting from contact of the surface of the skin with a sensitizing chemical. A murine model for contact sensitivity is widely used to develop therapies for chronic inflammation, autoimmune disorder, and organ transplant rejection (Goebeler, M., et al., Int Arch. Allergy Appl. Immunol., 1990, 93, 294–299). One example of such a disease is atopic dermatitis. Female Balb/c mice between the ages of 8 and 12 weeks are used to assess the activity of TNF-α antisense oligonucleotides in a contact sensitivity model.

Balb/c mice receive injections of oligonucleotide drug in saline via i.v. injection into the tail vein. The abdomen of the mice is shaved using an Oster hair clipper. The animals are anesthesized using isoflurane, and 25 µl of 0.2% 2,4-dinitrofluorobenzene (DNFB) in 4:1 acetone:olive oil is applied to the shaved abdomen two days in a row. After five days, 10 ml of 0.2% DNFB in the same vehicle is applied to the right ear. After each exposure, the mouse is suspended in air for two minutes to allow the DNFB to absorb into the skin. 24 and 48 hours after application of DNFB to the ear, the ear thickness is measured using a micrometer. Inflammation (dermatitis) is indicated by a ranked thickening of the ear. Thickness of the treated ear is compared to untreated (contralateral) ear thickness.

Example 11

Effect of Antisense Inhibition of TNF-α in a Murine Model for Crohn's Disease

C3H/HeJ, SJL/JK and IL10−/− mice are used in a TNBS (2,4,5,-trinitrobenzene sulfonic acid) induced colitis model for Crohn's disease (Neurath, M. F., et al., J. Exp. Med., 1995, 182, 1281–1290). Mice between the ages of 6 weeks and 3 months are used to assess the activity of TNF-α antisense oligonucleotides.

C3H/HeJ, SJL/JK and IL10−/− mice are fasted overnight prior to administration of TNBS. A thin, flexible polyethylene tube is slowly inserted into the colon of the mice so that the tip rests approximately 4 cm proximal to the anus. 0.5 mg of the TNBS in 50% ethanol is slowly injected from the catheter fitted onto a 1 ml syringe. Animals are held inverted in a vertical position for approximately 30 seconds.

Antisense oligonucleotides targeted to TNF-α or PKC-δ which inhibit TNF-α expression are administered either at the first sign of symptoms or simultaneously with induction of disease. Animals, in most cases, are dosed every day. Administration is by i.v., i.p., s.q., minipumps or intracolonic injection. Experimental tissues are collected at the end of the treatment regimen for histochemical evaluation.

Example 12

Effect of Antisense Inhibition of TNF-α in a Murine Model for Multiple Sclerosis Experimental autoimmune encephalomyelitis (EAE) is a commonly accepted murine model for multiple sclerosis (Myers, K. J., et al., *J. Neuroimmunol.,* 1992, 41, 1–8). SJL/H, PL/J, (SJL×PL/J)F1, (SJL×Balb/c)F1 and Balb/c female mice between the ages of 6 and 12 weeks are used to test the activity of TNF-α or PKC-δ antisense oligonucleotides.

The mice are immunized in the two rear foot pads and base of the tail with an emulsion consisting of encephalitogenic protein or peptide (according to Myers, K. J., et al., *J. of Immunol.,* 1993, 151, 2252–2260) in Complete Freund's Adjuvant supplemented with heat killed *Mycobacterium tuberculosis*. Two days later, the mice receive an intravenous injection of 500 ng *Bordatella pertussis* toxin and additional adjuvant.

Alternatively, the disease may also be induced by the adoptive transfer of T-cells. T-cells are obtained from the draining of the lymph nodes of mice immunized with encephalitogenic protein or peptide in CFA. The T cells are grown in tissue culture for several days and then injected intravenously into naive syngeneic recipients.

Mice are monitored and scored daily on a 0–5 scale for signals of the disease, including loss of tail muscle tone, wobbly gait, and various degrees of paralysis.

Example 13

Effect of Antisense Inhibition of TNF-α in a Murine Model for Pancreatitis

Swiss Webster, C57BL/56, C57BL/6 lpr and gld male mice are used in an experimental pancreatitis model (Niederau, C., et al., *Gastroenterology,* 1985, 88, 1192–1204). Mice between the ages of 4 and 10 weeks are used to assess the activity of TNF-α antisense oligonucleotides.

Caerulin (5–200 μg/kg) is administered i.p. every hour for one to six hours. At varying time intervals, the mice are given i.p. injection of avertin and bled by cardiac puncture. The pancreas and spleen are evaluated for histopathology and increased levels of IL-1β, IL-6, and TNF-α. The blood is analyzed for increased levels of serum amylase and lipase. TNF-α or PKC-δ antisense oligonucleotides are administered by intraperitoneal injection at 4 hours pre-caerulin injections.

Example 14

Effect of Antisense Inhibition of TNF-α in a Murine Model for Hepatitis

Concanavalin A-induced hepatitis is used as a murine model for hepatitis (Mizuhara, H., et al., *J. Exp. Med.,* 1994, 179, 1529–1537). It has been shown that this type of liver injury is mediated by Fas (Seino, K., et al., *Gastroenterology* 1997, 113, 1315–1322). Certain types of viral hepatitis, including Hepatitis C, are also mediated by Fas (*J. Gastroenterology and Hepatology,* 1997, 12, S223–S226). Female Balb/c and C57BL/6 mice between the ages of 6 weeks and 3 months are used to assess the activity of TNF-α antisense oligonuclectides.

Mice are intravenenously injected with oligonucleotide. The pretreated mice are then intravenously injected with 0.3 mg concanavalin A (Con A) to induce liver injury. Within 24 hours following Con A injection, the livers are removed from the animals and analyzed for cell death (apoptosis) by in vitro methods. In some experiments, blood is collected from the retro-orbital vein.

Example 15

Effect of Antisense Inhibition of TNF-α on Survival in Murine Heterotopic Heart Transplant Model To determine the therapeutic effects of TNF-α or PKC-δ antisense oligonucleotides in preventing allograft rejection, murine oligonucleotides are tested for activity in a murine vascularized heterotopic heart transplant model. Hearts from Balb/c mice are transplanted into the abdominal cavity of C3H mice as primary vascularized grafts essentially as described by Isobe et al., *Circulation* 1991, 84, 1246–1255. Oligonucleotide is administered by continuous intravenous administration via a 7-day Alzet pump. The mean survival time for untreated mice is usually approximately 9–10 days. Treatment of the mice for 7 days with TNF-α antisense oligonucleotides is expected to increase the mean survival time.

What is claimed is:

1. An antisense oligonucleotide having 8 to 30 nucleotide units specifically hybridizable with a nucleic acid encoding human PKC-δ and which is capable of modulating human PKC-δ expression.

2. The oligonucleotide of claim 1 specifically hybridizable with a translation initiation site or coding region.

3. The oligonucleotide of claim 1 wherein at least one of the intersugar linkages between nucleotide units of the oligonucleotide is a phophorothioate.

4. The oligonucleotide of claim 1 wherein at least one of the nucleotides comprises a modification on the 2' position of the sugar.

5. The oligonucleotide of claim 4 wherein the modification is a 2'-O-methoxyethyl modification.

6. The oligonucleotide of claim 1 comprising SEQ ID NO: 4, 5, 7, 9, 11, 13, 14, 15 or 16.

7. A pharmaceutical composition comprising the oligonucleotide of claim 1 or claim 6 and a pharmaceutically acceptable carrier or diluent.

8. A pharmaceutical composition comprising the oligonucleotide of claims 1 or 6 and a carrier.

9. A method of inhibiting the expression of human PKC-δ comprising contacting tissues or cells which express human PKC-δ in vitro with an effective dose of the oligonucleotide of claim 1 wherein expression of human PKC-δ is inhibited.

10. The method of claim 9 wherein said expression of human PKC-δ is abnormal expression.

11. A method of inhibiting hyperproliferation of cells comprising contacting hyperproliferating cells in vitro with an effective dose of the oligonucleotide of claim 1, whereby hyperproliferation of cells is inhibited.

12. A method of modulating the expression of human TNF-α in cells or tissue comprising contacting said cells or tissue in vitro with the oligonucleotide of claim 1.

13. The method of claim 12 wherein said tissue is adipose tissue.

14. A method of treating an animal having a disease or condition associated with TNF-α comprising administering to said animal a therapeutically or prophylactically effective amount of an oligonucleotide consisting of the sequence of SEQ ID NO: 19, wherein said disease or condition is diabetes or rheumatoid arthritis, contact hypersensitivity.

15. A method of reducing the blood glucose level in an animal comprising administering to said animal a therapeutically or prophylactically effective amount of an oligonucleotide consisting of the sequence of SEQ ID NO: 19.

* * * * *